United States Patent [19]

Joshua et al.

[11] Patent Number: 5,349,063

[45] Date of Patent: Sep. 20, 1994

[54] PANCREATIC IMAGING AGENTS

[75] Inventors: Alummoottil V. Joshua, Edmonton; John R. Scott, Ardrossan, both of Canada

[73] Assignee: Alberta Cancer Board, Edmonton, Canada

[21] Appl. No.: 546

[22] Filed: Jan. 4, 1993

Related U.S. Application Data

[63] Continuation of Ser. No. 673,228, Mar. 21, 1991, abandoned.

[51] Int. Cl.$^5$ ............... C07D 265/30; C07D 211/26; C07D 207/30
[52] U.S. Cl. .................... 544/162; 546/229; 546/232; 548/561
[58] Field of Search ............... 544/162; 548/561; 546/229, 232

[56] References Cited

U.S. PATENT DOCUMENTS 4,360,511 11/1982 Baldwin et al. .................. 564/373
4,430,319 2/1984 Blau et al. ...................... 564/373

OTHER PUBLICATIONS

Trampesch et al. Chem. Abstracts, vol. 98, No. 3, 13806x 1983.
"Gastroenterology: Pancreas", No. 558, vol. 27, No. 6, p. 1013 Yamamoto et al., 1986.
"A New Brain Perfusion Imaging Agent: [1-123-]HIPDM:N,N,N'-Trimethyl-N'-[2-Hydroxyl-3-Methyl-5-Iodobenzyl]-1,3-Propanediamine" Kung et al; The Journal Of Nuclear Medicine; pp. 66–72, 1987.
"Pancreas Accumulation Of Radioiodinated HIPDM in Mice and Rats", Yamamoto et al, vol. 26, No. 7, pp. 765–769, 1985.
"Human Pancreas Scintigraphy Using Iodine-123-Labeled HIPDM and SPECT", Yamamoto et al, pp. 1015-1019, 1989.

*Primary Examiner*—Johann Richter
*Assistant Examiner*—Joseph K. McKane
*Attorney, Agent, or Firm*—Bell Seltzer Park

[57] ABSTRACT

A novel group of radiolabelled diamines are provided, effective for pancreatic imaging and represented by the formula

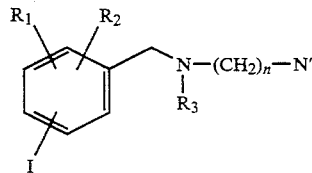

wherein n is 1 to 10; $R_1$ and $R_2$ are the same or different and are hydrogen, hydroxyl or lower alkyl having 1 to 6 carbon atoms; $R_3$ is lower alkyl having 1 to 6 carbon atoms; and N' is a nitrogen atom forming part of a 4- to 8-membered heterocyclic ring containing one or two hetero atoms, one of which is said nitrogen, said heterocyclic ring being unsubstituted or substituted with one or more lower alkyl groups and pharmaceutically acceptable acid addition salts thereof.

12 Claims, 3 Drawing Sheets

PANCREATIC IMAGING AGENTS

This application is a continuation, of application Ser. No. 07/673,228, filed Mar. 21, 1991 now abandoned.

FIELD OF INVENTION

This invention relates to nuclear medicine techniques for imaging body tissues and organs. In particular, this invention relates to compounds and methods useful for imaging of the pancreas.

BACKGROUND OF THE INVENTION

Scintigraphic investigations of pancreatic diseases have in the past primarily utilised radiolabelled amino acids, such as C-11-L-tryptophan which has been used in positron emission tomographic (PET) studies or amino acid analogues such as selenium-75 labelled selenomethionine which has been used for planar gamma camera imaging. The use of Se-75 selenomethionine has been largely discontinued due to the high patient radiation dose associated with selenium-75 and the inconsistency of pancreatic visualisation, due in part to the relatively small quantities of this material which could be administered.

U.S. Pat. No. 4,360,511 to Baldwin et al. disclosed radioiodinated monoamine compounds which locate primarily in the brain and are useful as brain imaging agents.

Although these compounds were described as accumulating in some degree in pancreas, no data were provided on localisation of these compounds in pancreas and other abdominal organs so that it was not possible to predict their suitability for pancreatic imaging.

Kung and co-workers developed certain radioiodinated diamines, including N,N,N'-trimethyl-N'[2-hydroxy-3-methyl-5-iodobenzyl]-1,3-propanediamine (HIPDM), as indicators of brain blood flow and as brain imaging agents (Kung et al., 1983, J. Nucl. Med., Vol. 24, p. 66; U.S. Pat. No. 4,430,319 to Blau et al.)

Yamamoto's group has found some localisation of HIPDM in the pancreas of rats and mice but human clinical studies with this compound have proved disappointing in that differentiation between pancreatic and liver retention of the compound was difficult and pancreas/liver ratios are not optimal for clinical use. (Yamamoto et al., (1985), J. Nucl. Med., Vol. 26, p. 764; (1986), J. Nucl. Med., Vol. 27, p. 1013; (1990) J. Nucl. Med., Vol. 31, p. 1015).

There remains a need for convenient and discriminating pancreatic imaging agents suitable for routine diagnostic use.

SUMMARY OF THE INVENTION

In accordance with one aspect of the invention, compounds are provided effective for pancreatic imaging having the general formula:

wherein n is 1 to 10; $R_1$ and $R_2$ are the same or different and are hydrogen, hydroxyl or lower alkyl having 1 to 6 carbon atoms; $R_3$ is lower alkyl having 1 to 6 carbon atoms; and N' is a nitrogen atom forming part of a 4- to 8-membered heterocyclic ring containing one or two hetero atoms, one of which is the nitrogen, the heterocyclic ring being unsubstituted or substituted with one or more lower alkyl groups and pharmaceutically acceptable acid addition salts thereof.

According to a further aspect of the invention a process is provided for the preparation of a compound effective for pancreatic imaging having the general formula:

wherein n is 1 to 10; $R_1$ and $R_2$ are lower alkyl having 1 to 6 carbon atoms; and N' is a nitrogen atom forming part of a 4- to 8-membered heterocyclic ring containing one or two hetero atoms, one of which is the nitrogen, the heterocyclic ring being unsubstituted or substituted with one or more lower alkyl groups comprising the steps of:

(a) reacting appropriately substituted phenol with HCHO/anhydrous $SnCl_4$ to produce the corresponding benzaldehyde;

(b) iodinating the resulting benzaldehyde by reacting it with iodopyridinium nitrate to give the corresponding iodobenzaldehyde;

(c) condensing the iodobenzaldehyde produced by step (b) with an amine having the desired substituents to form the corresponding imine;

(d) reducing the imine with sodium borohydride in ethanol; and (e) reductively alkylating the product of step (d) to give the desired N-alkyl derivative.

According to a further aspect of the invention, a method is provided for imaging the pancreas of a mammal comprising administering an effective amount of a compound effective for pancreatic imaging having the general formula:

wherein n is 1 to 10; $R_1$ and $R_2$ are the same or different and are hydrogen, hydroxyl or lower alkyl having 1 to 6 carbon atoms; $R_3$ is lower alkyl having 1 to 6 carbon atoms; and N' is a nitrogen atom forming part of a 4- to 8-membered heterocyclic ring containing one or two hetero atoms, one of which is the nitrogen, the heterocyclic ring being unsubstituted or substituted with one or more lower alkyl groups and pharmaceutically acceptable acid addition salts thereof in a suitable carrier to the mammal so that the compound is distributed to and entrained in the pancreas and subsequently detecting radiation emitted from the compound in the pancreas.

According to a further aspect of the invention, a method is provided for imaging the pancreas of a mammal comprising administering an effective amount of I-123 N[3(1-diethylamino)propyl]-N-methyl-2-hydroxy-3-methyl-5-iodobenzylamine or a pharmaceutically acceptable acid addition salt thereof in a suitable carrier to the mammal so that the compound is distributed to and entrained in the pancreas and subsequently detecting radiation emitted from the compound in the pancreas.

The invention, as exemplified by preferred embodiments, is described with reference to the drawings in which.

DETAILED DESCRIPTION OF THE INVENTION

The invention provides a novel group of radiolabelled diamines useful for imaging of the pancreas in humans.

In order to be an effective agent for pancreatic imaging, a compound must not only be taken up by the pancreas in sufficient amounts, but must show sufficient differential localisation in the pancreas, compared to its localisation in other abdominal organs such as the liver, to permit satisfactory pancreatic images to be obtained without interference from other organs.

U.S. Pat. No. 4,430,319 discloses agents, including HIPDM, useful as brain imaging agents because of their accumulation in brain. Kung did not disclose any information on uptake of these compounds in pancreas.

As used herein, "effective for pancreatic imaging" means that a compound has a pancreatic uptake of at least approximately 4.5% of the administered radioactive dose at some point within 24 hours of administration and the pancreas/liver uptake ratio should be at least approximately 1.5 at that time.

The novel diamine compounds of the invention are superior to HIPDM both in pancreatic uptake and in pancreas/liver uptake ratio, thereby providing a superior diagnostic tool permitting use of lower patient radiation doses or, at comparable dose rate, providing superior diagnostic images.

As used herein, "lower alkyl" denotes a straight or branched chain alkyl radical having 1 to 6 carbon atoms. Preferred lower alkyl radicals are methyl and ethyl.

In the substituted benzene ring of formula I, $R_1$ and $R_2$ are the same or different and are hydrogen, hydroxyl or lower alkyl. The preferred configurations for the benzene ring are 2-hydroxy, 3-lower alkyl, 5-iodo or 2-hydroxy, 3-iodo, 5-lower alkyl, the former being especially preferred.

In formula I, N' is preferably a nitrogen forming part of a 5- or 6-membered ring containing one or two hetero atoms, one of which is the nitrogen. The second hetero atom, if present, is preferably oxygen. Preferred values for n are 2, 3 or 4.

Preferred iodinated diamines in accordance with the present invention include N[3(4-morpholino)propyl]-N-methyl-2-hydroxy-3-methyl-5-iodobenzylamine (ERC 9); N[3(1-Pyrrolidino)propyl]-N-methyl-2-hydroxy-3-methyl-5-iodobenzylamine (ERC 46); and N[3(1-piperidino)propyl]-N-methyl-2-hydroxy-3-methyl-5-iodobenzylamine (ERC 90).

ERC 9 is an especially preferred embodiment of the invention.

Figure 1:
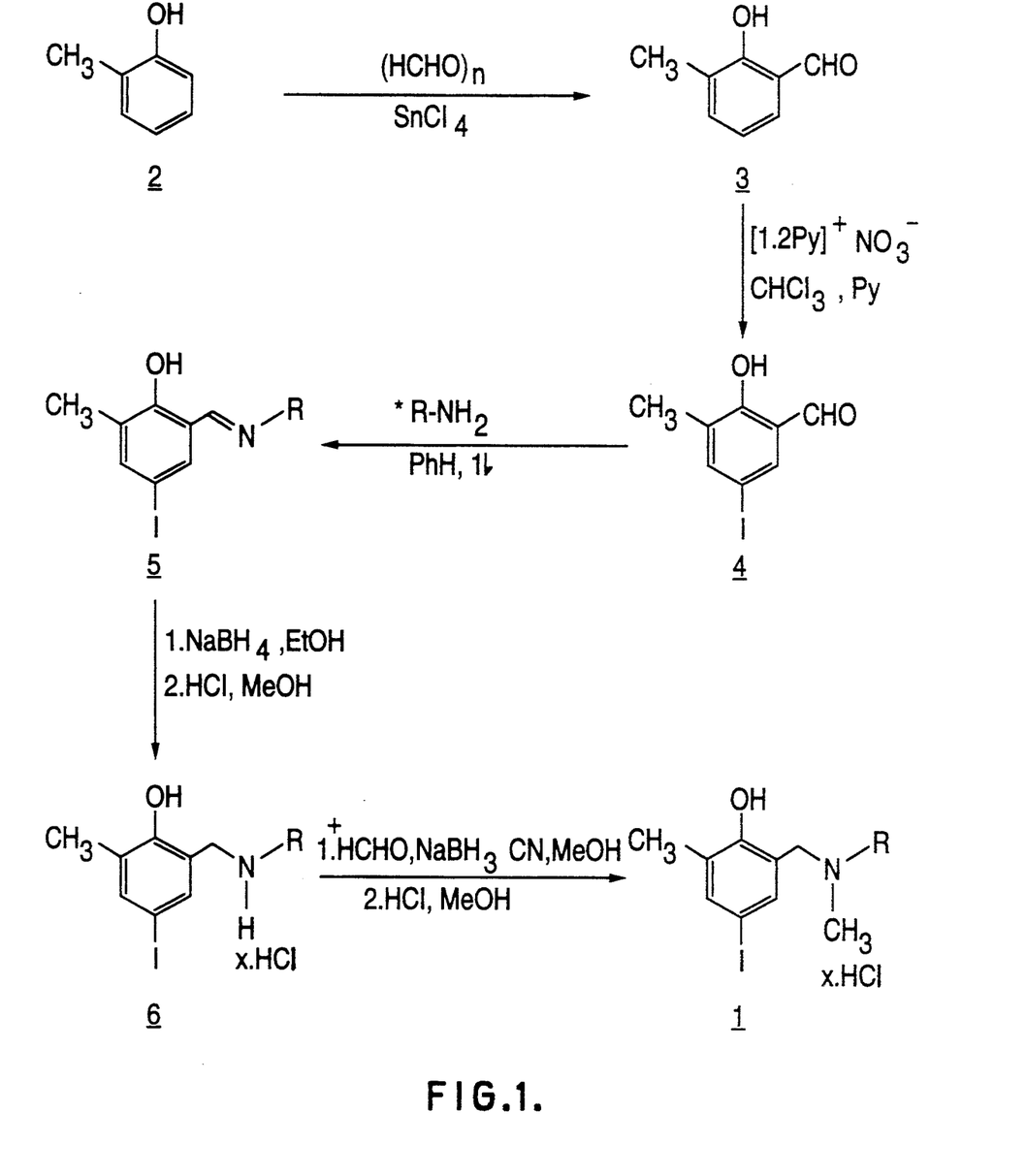
FIG. 1 shows a flow-chart of the process for preparation of the compounds of the invention; *R represents —$(CH_2)_n$—N' where N' is a suitable amine group; Acetaldehyde for ethyl and acetone for isopropyl.

The compounds of the invention were synthesised using a modification of the method of Tramposch (1983, J. Med. Chem., vol. 26, p. 121), as set out in the flow chart of FIG. 1 and as exemplified in Examples 1 to 5.

For iodination of the phenolic aldehyde, 3, iodopyridinium nitrate was used instead of iodine monochloride in acetic acid. Iodopyridinium nitrate was generated from iodine monochloride and silver nitrate in chloroform-pyridine by the method of Lown & Joshua (Can. J. Chem. (1977), Vol. 55, p. 122).

The iodoaldehyde, 4, was condensed with the desired amines in refluxing benzene to form the imines, 5, which were reduced with sodium borohydride in ethanol. The products, 6, were purified by conversion to the dihydrochlorides and crystallisation from methanol-acetone. The N-alkyl derivatives, 1, were prepared by reductive alkylation with the appropriate aldehyde or ketone (formaldehyde for methyl, acetaldehyde for ethyl, acetone for isopropyl etc.) in methanol and purified as the dihydrochlorides.

Radiolabelling of the compounds of the invention was achieved by exchange, by heating the compound of interest with radioiodine in the form of sodium iodide in the presence of acetic acid in a boiling water bath for 30 minutes followed by neutralization with sodium hydroxide. Radiochemical purity was above 95% without further purification.

Although specific methods of preparation of the compounds of the invention have been described, it is within the invention to form the compounds by any suitable method.

The invention includes compounds labelled with any radioisotope of iodine, including I-121, I-123, I-125 and I-131. The preferred isotope for imaging in humans is I-123.

The compounds of the invention labelled with I-121 may be employed in PET techniques.

To determine that a compound is effective for pancreatic imaging, its pancreatic uptake and pancreas/liver uptake ratio is determined in mice as described in Example 6.

For use in pancreatic imaging, the radiolabelled compounds of the invention are prepared as sterile, pyrogen-free products by conventional techniques known to those skilled in the art. They are administered by intravenous injection and pancreatic uptake and pancreas/liver uptake ratio are preferably assessed approximately 3 to 4 hours after administration.

Imaging of the pancreas may be done by conventional gamma camera imaging methods, with or without single photon emission computed tomography (SPECT) capability, such methods being well known to those skilled in the art.

If the compounds of the invention are labelled with I-121, the compounds may be used for pancreatic imaging by position emission tomography (PET).

High quality pancreatic images, shown in FIGS. 2 and 3, have been obtained in human volunteers using the preferred embodiment of the invention, ERC 9, as described in Example 11.

According to a further embodiment of the invention, the diamine N[3(diethylamino)propyl]-N-methyl-2-hydroxy-3-methyl-5-iodobenzylamine (ERC 94) was shown to be effective for pancreatic imaging. The corresponding dimethyl compound, HIPDM, has proved unsatisfactory for clinical use, as described above but, unexpectedly, ERC 94, the diethyl compound, was found to be effective for pancreatic imaging.

The compounds of the invention, and especially the preferred embodiment ERC 9, provide convenient radiodiagnostic agents for imaging the pancreas using conventional, readily available gamma cameras, thus providing a routine clinical method which will increase diagnostic accuracy in pancreatic diseases, including pancreatitis and pancreatic cancers.

EXAMPLE 1

Synthesis of N[3-Morpholino)propyl]-N-methyl-2-hydroxy-3-methyl-5-iodobenzylamine Dihydrochloride (ERC 9)

a. Preparation 2-Hydroxy-3-methylbenzaldehyde

To a solution of o-cresol (Fisher, 21.6 g, 200 mmol) and tributylamine (Eastman, 14.8 g, 80 mmol) in toluene (100 ml) under a nitrogen atmosphere was added anhydrous stannic chloride (5.2 g, 20 mmol) dropwise over 5 min. The mixture was stirred at room temperature for 30 min. Paraformaldehyde (Aldrich, 13.2 g, 440 mmol) was added and the resulting suspension was heated at 95° C. for 20 h. The mixture was allowed to cool and poured into water (2 L). The mixture was acidified to pH2 with conc. hydrochloric acid and extracted with ether (2×200 ml). The combined extracts were washed with water (100 ml), dried ($Na_2SO_4$) and evaporated. The residual oil was distilled under vacuum, to yield the title compound containing about 30% starting material. Yield 20.6 g; bp. 64°–69° C. (3.5 Torr). Without further purification this material was used in the next step.

b. Preparation of 2-Hydroxy-3-methyl-5-iodobenzylaldehyde

Silver nitrate (BDH, 39.42 g, 232 mmol) was dissolved in a mixture of chloroform (280 mL) and pyridine (120 ml). To this stirred solution iodine monochloride (Aldrich, 37,68 g, 232 mmol) in chloroform (40 ml) was added dropwise over 30 min. The mixture was stirred for another 15-20 min. To this stirred mixture 2-hydroxy-3-methylbenzaldehyde (20.6 g, containing approximately 30% o-cresol) was added dropwise (10 min). The mixture was stirred at room temperature for 20 h. The reaction mixture was diluted with ether (approximately 600 ml) to precipitate the pyridinium nitrate and filtered. The precipitate was washed several times with ether. The combined filtrates were evaporated under vacuum. The residue was extracted several times with hexane and the combined extracts concentrated on a rotary evaporator to yield a brown solid. The product was chromatographed on silica gel and eluted with hexane-dichloromethane (4:1). Crystallization from hexane gave the title compound as yellow crystals. Yield, 27 g; mp. 85°–86° C. NMR ($CDCl_3$): δ2.3 (S, 3H, —$CH_3$), 7.8 (s, 2H, aromatic H), 9.93 (s, 1H, —CHO), 11.3 (s, 1H, —OH).

c. Preparation of N[3-(4-Morpholino)propyl]-2-hydroxy-3-methyl-5-iodobenzylamine Dihydrochloride A mixture of 2-hydroxy-3-methyl-5-iodobenzaldehyde (5.24 g, 20 mmol), N-(3-aminopropyl)morpholine (Aldrich, 2.88 g, 20 mmol) and benzene (150 ml) was refluxed under a Dean-Stark head to separate water (2 h). The solvent was evaporated under reduced pressure to give a yellow oil. The oil was dissolved in ethanol (50 ml), sodium borohydride (BDH, 0.76 g, 20 mmol) was added and stirred at room temperature for 20 h. Most of the ethanol was removed under vacuum, the residue was taken up in deionized water (50 ml) and extracted with dichloromethane (5 ×30 ml). The combined extracts were washed with deionized water (30 ml), dried ($Na_2SO_4$) and the solvent removed under vacuum. The residual oil was dissolved in methanol (50 ml), acidified with conc. hydrochloric acid (10 ml) and evaporated to dryness. The residue was crystallized from methanol-acetone to yield 9.18 g (99%) of the title compound as colorless crystals. mp. 194°–195° C.(d). NMR($CDCl_3$ Free base): δ1.57–1.87 (m, 2H, —$CH_2$), 2.2 (s, 3H, —$CH_3$), 2.33–2.53 (m, 6H, N—$CH_2$), 2.73 (t, 2H, J=6 Hz, N—$CH_2$), 3.63–3.83 (m, 4H, $CH_2$—O), 3.93 (s, 2H, benzylic $CH_2$), 6.7 (bs, 2H, NH, OH), 7.16 (d, 1H, J=1 Hz, aromatic H); 7.36(d, 1H, J=1 Hz, aromatic H) . IR (KBr): 3420, 3180, 2940, 2670, 2600, 1625, 1480, 1440, 1390, 1270, 1210, 1105, 870, $cm^{-1}$. Analysis found: C, 39.03; H, 5.44; N, 6.05 $C_{15}H_{25}Cl_2IN_2O_2$ requires: C, 38.90; H, 5.44; N, 6.05.

d. Preparation of N[3(4-Morpholino)propyl-N-methyl-2-hydroxy-3-methyl-5-iodobenzylamine Dihydrochloride To a stirred solution of the diamine dihydrochloride above (9.18 g, 19.8 mmol) and formaldehyde (Fisher, 37% solution, 10 ml), in methanol (100 ml) at 0° C., sodium cyanoborohydride (aldrich 1.89 g, 30 mmol) was added in portions (5 min). The solution was allowed to warm to room temperature slowly and stirred for 72 h. Most of the methanol was evaporated under reduced pressure. The residual oil taken up in deionized water (100 ml), treated with solid sodium bicarbonate (3 g) to neutralize excess hydrochloric acid and extracted with dichloromethane (5×30 ml). The combined extracts were washed with deionized water (30 ml), dried ($Na_2SO_4$) and evaporated. The residual oil was taken up in methanol (50 ml), treated with conc. hydrochloric acid (10 ml) and evaporated to dryness in vacuo. The product was recrystallized from methanol-acetone. Yield: 9.1 g (99%); mp. 194°–195° C. (d) . NMR ($CDCl_3$, free base): δ1.6—2.0 (m, 2H, —$CH_2$—): 2.2 (s, 3H, —$CH_3$), 2.33 (s, 3H, $CH_3$), 2.3–2.8 (m, 8H, N—$CH_2$), 3.6–3.9 (m, 6H, $CH_2$—O, benzylic $CH_2$), 7.17 (d, 1H, J=1 Hz, aromatic H), 7.4 (d, 1H, J=1 Hz, aromatic H), 10.1 (bs, 1H, —OH), IR (KBr): 3420, 2950, 2640, 1640, 1465, 1385, 1265, 1205, 1105 $cm^{-1}$. Analysis found: C, 40.00; H, 5.68; N, 5.71. $C_{16}H_{27}Cl_2IN_2O_2$ requires: C, 40.27; H, 5.70, N, 5.87.

EXAMPLE 2

Radiolabelling of ERC 9

2 mg of the product prepared as in Example 1,100 μl glacial acetic acid, 400 μl distilled water and 1–15 MBq I-125, 1–50 MBq I-131 or 100–200 MBq I-123 sodium iodide were heated in a sealed vial in a boiling water bath for 30 minutes, followed by neutralisation by addition of 0.6 ml of 1N sodium hydroxide. The preparation was diluted to the desired concentration with 0.9% sodium chloride in water.

Radiochemical purity was assessed by thin layer chromatography (Kodak* Chromagram Silica Gel) using ethyl acetate-ethanol (1:1) as the developing solvent. In this system radioiodinated ERC 9 has a Rf of 0.1–0.3 while radioiodine sodium iodide has a Rf of 0.8–1.0. Radiochemical purity was consistently above 95%.

EXAMPLE 3

Synthesis of N[3(1-Pyrrolidino)propyl]-N-methyl-2-hydroxy-3-methyl-5-iodobenzylamine Dihydrochloride (ERC 46)

a. Preparation of N-(3-Aminopropyl)pyrrolidine

A mixture of pyrrolidine (Aldrich, 7.1 g, 100 mmol), acrylonitrile (BDH, 7.96 g, 150 mmol) and ethanol (25 ml) was stirred at room temperature for 20 hours. The solvent was removed by evaporation under vacuum to give N-pyrrolidinopropionitrile in almost quantitative yield. This material was used in the next step without purification.

To a stirred suspension of lithium aluminum hydride (Alfa Products 4 g, 100 mmol) in anhy tetrahydrofuran (150 ml) under nitrogen, a solution of the above nitrile in THF (25 ml) was added dropwise (2 h). The mixture was refluxed under nitrogen for 20 h. Excess lithium aluminum hydride was discharged by the dropwise addition of water (25 ml) in THF (30 ml), stirred for another 30 minutes and filtered. The filter cake was washed several times with THF-methanol (1:1). The combined filtrates were evaporated under reduced pressure and the residue distilled under vacuum to yield N-(3-aminopropyl)pyrrolidine. Yield 4.5 g (35%); bp. 54°–55° (5.5 Torr.). [lit.bp. 85°–87° C. (26 Torr., J. Corse et al., J. Amer. Chem. Soc., 68, 1911 (1946)].

b. Preparation of N[3(1-Pyrrolidino)propyl]-2-hydroxy-3-methyl-5-iodobenzylamine Dihydrochloride Reaction of 2-hydroxy-3-methyl-5-iodobenzaldehyde (1.048 g, 4 mmol) with N-(3-aminopropyl)pyrrolidine (0.512 g, 4 mmol) in benzene (60 ml), reduction of the resulting imine with sodium borohydride (0.160 g, 4 mmol) in ethanol (20 ml), work-up conversion to the dihydrochloride (conc. hydrochloric acid, 4 ml), evaporation to dryness, and crystallization of the residue from methanol-acetone as described for Example 1 gave the title compound as an off-white solid. Yield: 1.685 g (94%); mp. 183°–186° C. (d). NMR (CDCl$_3$, free base): δ1.5–2.0 (m, 6H, —CH$_2$—), 2.13 (s, 3H, —CH$_3$), 2.4–2.8 (m, 8H, N—CH$_2$), 3.9 (s, 2H, benzylic CH$_2$), 6.7 (bs, 2H, NH, OH), 7.1 (d, 1H, J=1 Hz, aromatic H), 7.3 (d, 1H, J=1 Hz, aromatic H) IR(KBr): 3430, 2960, 2700, 1625, 1475, 1390, 1215 cm$^{-1}$ Analysis found: C, 40.06; H, 5.86; N, 6.05 C$_{15}$H$_{25}$Cl$_2$IN$_2$O requires: C, 40.29; H, 5.64; N, 6.26 c. Preparation of N[3-(1-Pyrrolidino)propyl]-N-methyl-2-hydroxy-3-methyl-5-iodobenzylamine Dihydrochloride Reductive methylation of N[3(1-pyrrolidino)propyl]-2-hydroxy-3-methyl-5-iodobenzylamine dihydrochloride 0.894 g, 2 mmol) with formaldehyde (2 mL, 37% solution) and sodium cyanoborohydride (0.252 g, 4 mmol) in methanol (10 mL), work-up, conversion to the dihydrochloride (conc. hydrochloric acid, 2 mL) and crystallization from methanol-acetone as described for Example 1, gave the title compound as colorless crystals. Yield: 0.919 g (99%), mp. 190°–192° C. (d). NMR (CDCl$_3$, free base): δ1.7–2.2 (m, 6H, —CH$_2$—); 2.23 (s, 3H, —CH$_3$; 2.33 (s, 3H, —CH$_3$); 2.43–2.8 (m, 8H, N—CH$_2$); 3.7 (s, 2H benzylic CH$_2$), 7.2 (d, 1H, J=1 Hz, aromatic H) , 7.4 (d, 1H, J=1 Hz, aromatic H); 10.43 (s, 1H, —OH). IR (KBr): 3420, 3220, 2960, 2670, 2600, 2500, 1620, 1470, 1385, 1200 cm$^{-1}$ Analysis found: C, 41.67; H, 5.97; N, 5.97. C$_{16}$H$_{27}$Cl$_2$IN$_2$O requires: C, 41.67; H, 5.90; N, 6.07.

EXAMPLE 4

Synthesis of N[3(1-Piperidino)propyl]-N-methyl-2-hydroxy-3-methyl-5-iodobenzylamine Dihydrochloride (ERC 90)

a. Preparation of N-(3-Aminopropyl)piperidine

Reaction of piperidine (Aldrich, 8.4 g, 100 mmol) with acrylonitrile (7.96 g, 150 mmol) in ethanol (25 mL), reduction of the resulting piperidinopropionitrile with lithium aluminum hydride (5 g, 125 mmol) in tetrahydrofuran (150 mL), work-up and distillation under reduced pressure as described for Example 3 gave the title compound. Yield: 3 g (21%); bp. 65°–66° (6 Torr); [lit. bp. 110°–115° C. (31 Torr), J. Corse et al., J. Amer. Chem. Soc., 68, 1911 (1946)].

b. Preparation of N[3(1-Piperidino)propyl]-2-hydroxy-3-methyl-5-iodobenzylamine Dihydrochloride Reaction of 2-hydroxy-3-methyl-5-iodo-benzaldehyde (0.524 g, 2 mmol) with N-(3-aminopropyl)piperidine (0.284 g, 2 mmol) in benzene (60 mL), reduction of the resulting imine with sodium borohydride (0.16 g, 4 mmol) in ethanol (25 mL), work-up, conversion to the dihydrochloride (conc. hydrochloric acid, 2 mL), evaporation to dryness and crystallization from methanol-acetone as described for Example 1 gave the title compound as a colorless solid. Yield: 0.82 g (89%); mp. 201°–203° C. (d). NMR (CDCl$_3$, free base): δ1.2–1.9 (m, 8H, —CH$_2$—); 2.2 (s, 3H, —CH$_3$); 2.27–2.53 (m, 6H, N—CH$_2$); 2.73 (t, 2H, J=6 Hz, NH—CH$_2$); 3.93 (s, 2H benzylic CH$_2$), 7.17 (d, 1H, J=1 Hz, aromatic H); 7.4 (d, 1H, J=1 Hz, aromatic H); NH and OH appear as a broad inflection above the baseline between δ5.7 and 7.9 IR (KBr): 3430, 2950, 2720, 1605, 1480, 1390, 1240, 1200, 1180, 870 cm$^{-1}$. Analysis found: C, 41.49; H, 5.94; N, 5.92. C$_{16}$H$_{27}$Cl$_2$IN$_2$O requires: C, 41.67; H, 5.90; N, 6.07.

c. Preparation of N[3-(1-Piperidino)propyl]-N-methyl-2-hydroxy-3-methyl-5-iodobenzylamine Dihydrochloride Reductive methylation of N[3(1-piperidino)propyl]-2-hydroxy-3-methyl-5-iodobenzylamine dihydrochloride 0.463 g, 1 mmol) with formaldehyde (1 mL, 37% solution) and sodium cyanoborohydride (0.126 g, 2 mmol) in methanol (10 mL), work-up, conversion to the dihydrochloride (conc. hydrochloric acid, 1 mL) and crystallization from methanol-acetone as described for Example 1 gave the title compound as colorless solid. Yield: 0,467 g (98%), mp. 200°–203° C.(d). NMR (CDCl$_3$, free base): δ1.2–1.9 (m, 8H, m, —CH$_2$—); 2.0–2.7 [2s (2.15 and 2.25) over a multiplet, 14H, —CH$_3$; N—CH$_2$ ]; 3.6 (s, 2H benzylic CH$_2$), 7.13 (d, 1H, J=1 Hz, aromatic H), 7.37 (d, 1H, J=1 Hz, aromatic H). IR (KBr): 3420, 2950, 2680, 1620, 1485, 1390, 1210 cm$^{-1}$ Analysis found: C, 42.96; H, 6.22; N, 5.98. C$_{17}$H$_{29}$Cl$_2$IN$_2$O requires: C, 42.96; H, 6.15; N, 5.89.

EXAMPLE 5

Synthesis of N[3(1-Diethylamino)propyl]-N-methyl-2-hydroxy-3-methyl-5-iodobenzylamine Dihydrochloride (ERC 94)

a. Preparation of N-(3-Diethylamino)propyl]-2-hydroxy-3-methyl-5-iodobenzylamine Dihydrochloride Condensation of 2-hydroxy-3-methyl-5-iodobenzaldehyde (1.31 g, 5 mmol) with 3-(diethylamino)-propylamine (Aldrich, 0.65 g, 5 mmol) in benzene (80 mL), reduction of the resulting imine with sodium borohydride (0.4 g, 10 mmol) in ethanol (25 mL), work-up, conversion to the dihydrochloride (conc. hydrochloric acid, 5 mL) and evaporation to dryness in vacuo as described in Example 1 gave the title compound as a hydroscopic foam. Without purification, this material was used in the next step. NMR (CDCl$_3$, free base): $\delta$1.05 (t, 6H, J=6 Hz, CH$_2$—CH$_3$), 1.53–1.9 (m, 2H, —CH$_2$—); 2.23 (s, 3H, —CH$_3$); 2.4–2.9 (m, 8H, —N—CH$_2$); 3.96 (s, 2H benzylic CH$_2$), 7.2 (d, 1H, J=1 Hz, aromatic H); 7.43 (d, 1H, J=1 Hz, aromatic H); NH and OH appear as an inflection above the base-line between $\delta$5.5 and 7.9.

b. Preparation of N[3(Diethylamino)propyl]-N-methyl-2-hydroxy-3-methyl-5-iodobenzylamine Dihydrochloride Reductive methylation of N[3(Diethylamino)-propyl]-2-hydroxy-3-methyl-5-iodo-benzylamine dihydrochloride (5 mmol, from last step) formaldehyde (5 mL, 37% solution) and sodium cyanoborohydride (0.63 g, 10 mmol) in methanol (25 mL), work-up, conversion to the dihydrochloride (conc. hydrochloric acid, 5 mL), evaporation to dryness in vacuo and crystallization of the resulting material from methanol-acetone as described for Example 1 gave the title compound as colorless crystals. Yield(overall): 1,945 g (84%); mp. 166°–168° C. NMR (CDCl$_3$, free base): $\delta$0.97 (t, 6H, J-6 Hz, —CH$_2$—CH$_3$); 1.5–1.9 (m, 2H, —CH$_2$—); 2.13 (s, 3H, —CH$_3$); 2.23 (s, 3H, —CH$_3$); 2.3–2.7 (m, 8H, N—CH$_2$); 3.6 (s, 2H benzylic CH$_2$), 7.1 (d, 1H, J=1 Hz, aromatic H); 7.35 (d, 1H, J=1 Hz, aromatic H); IR (KBr): 3420, 2940, 2640, 1625, 1470, 1390, 1210 cm$^{-1}$. Analysis found: C, 41.47; H, 6.24; N, 5.93. C$_{16}$H$_{29}$Cl$_2$IN$_2$O requires: C, 41.49; H, 6.31; N, 6.05.

EXAMPLE 6

Pancreatic Uptake of ERC-9

The pancreatic uptake and pancreas/liver ratio of I-125 ERC 9 (prepared as in Examples 1 and 2) and I-125-HIPDM were compared in mice. Male Balb/c mice were injected via the tail vein with I-125 ERC 9 or I-125 HIPDM (20 $\mu$g, 0.01 MBq, in 0.1 ml). At specific time periods from 5 minutes to 24 hours after administration, six mice from each group were killed by CO$_2$ asphyxiation. Blood samples were taken and various organs (including the pancreas and liver) were removed. The radioiodine uptake in various organs was determined by counting in a gamma spectrometric detector. The amount of radioactivity in each organ or tissue was compared to that in a standard of the injected dose. The percent uptake was calculated for each organ of each animal. The pancreas to liver ratio was calculated by dividing the percent uptake in the pancreas by the percent uptake in the liver. The mean uptake in the organs and the mean pancreas/liver ratio was calculated for the animals at each time period.

The results for the uptake in the pancreas and the pancreas/liver ratios are shown in Table 1.

TABLE 1

Pancreas Uptake and Pancreas to Liver Ratio in Balb/c Mice
(Six animals at each time period)

| Time After Administration | ERC 9 Pancreas | ERC 9 P/L # | HIPDM Pancreas | HIPDM P/L # |
|---|---|---|---|---|
| 5 Minutes | 2.08 ± 0.90 | 0.40 ± 0.10+ | 2.64 ± 0.50 | 0.21 ± 0.03 |
| 30 Minutes | 4.52 ± 0.75 | 0.61 ± 0.05+ | 3.87 ± 0.44 | 0.32 ± 0.04 |
| 1 Hour | 4.79 ± 0.70 | 0.66 ± 0.14+ | 5.12 ± 0.65 | 0.46 ± 0.06 |
| 4 Hours | 6.60 ± 1.84 | 2.02 ± 0.67+ | 5.12 ± 0.59 | 0.95 ± 0.14 |
| 24 Hours | 3.30 ± 0.53 | 2.54 ± 0.34+ | 2.46 ± 0.88 | 1.18 ± 0.47 |

*Mean percent administered dose per organ ± standard deviation
Mean of percent injected dose in pancreas/Percent injected does in liver ± standard deviation
+Significantly different from HIPDM at p $\leq$ 0.5

At all time intervals, the mean pancreas/liver ratio for ERC 9 is greater than that for HIPDM, permitting improved differentiation between pancreas and liver by use of I-123 ERC 9 as an imaging agent.

EXAMPLE 7

Pancreatic Uptake of ERC 46

The pancreatic uptake and pancreas/liver ratios of I-125 ERC 46 and I-125 HIPDM were compared in Balb/c mice as described in Example 6. The results are shown in Table 2.

Although the pancreas uptake was lower with ERC 46 at early time periods, at 4 and 24 hours after administration, ERC 46 had higher pancreas uptake than did HIPDM. At all time periods studied from 30 minutes to 24 hours, the pancreas/liver ratios were significantly higher with ERC 46.

EXAMPLE 8

Pancreatic Uptake of ERC 90

The pancreas uptake and pancreas/liver ratios of I-125 ERC 90 and I-125 HIPDM were compared in Balb/c mice as described in Example 6. The results are shown in Table 3.

Although the pancreas uptakes were lower with ERC 90 at early time periods, at 4 and 24 hours after administration ERC 90 had higher pancreas uptakes than did HIPDM. At all time periods studied from 30 minutes to 24 hours, the pancreas/liver ratios were significantly higher with ERC 90.

TABLE 2

Pancreas Uptake and Pancreas to Liver Ratio in Balb/c Mice
(Six Animals at Each Time Period)

| Time After Administration | ERC 46 Pancreas* | ERC 46 P/L# | HIPDM Pancreas* | HIPDM P/L# |
|---|---|---|---|---|
| 5 Minutes | 1.34 ± 0.32+ | 0.22 ± 0.04 | 2.64 ± 0.50 | 0.21 ± 0.03 |
| 30 Minutes | 4.14 ± 0.68 | 0.54 ± 0.09+ | 3.87 ± 0.44 | 0.32 ± 0.04 |
| 1 Hour | 3.74 ± 0.69+ | 0.78 ± 0.20+ | 5.12 ± 0.65 | 0.46 ± 0.06 |
| 4 Hours | 5.95 ± 0.78 | 2.11 ± 0.32+ | 5.12 ± 0.59 | 0.95 ± 0.14 |

TABLE 2-continued

Pancreas Uptake and Pancreas to Liver Ratio in Balb/c Mice
(Six Animals at Each Time Period)

| Time After Administration | ERC 46 | | HIPDM | |
| --- | --- | --- | --- | --- |
| | Pancreas* | P/L# | Pancreas* | P/L# |
| 24 Hours | 4.91 ± 0.43+ | 7.47 ± 1.40+ | 2.46 ± 0.88 | 1.18 ± 0.47 |

*Mean Percent of Administereed Dose Per Organ ± Standard Deviation
Mean of Percent Administered Dose in Pancreas/Percent Injected Dose in Liver ± Standard Deviation
+Significantly Different from HIPDM at p ≤ 0.05

TABLE 3

Pancreas Uptake and Pancreas to Liver Ratio in Balb/c Mice
(Six Animals at Each Time Period)

| Time After Administration | ERC 90 | | HIPDM | |
| --- | --- | --- | --- | --- |
| | Pancreas* | P/L# | Pancreas* | P/L# |
| 5 Minutes | 1.32 ± 0.34+ | 0.22 ± 0.04 | 2.64 ± 0.50 | 0.21 ± 0.03 |
| 30 Minutes | 2.73 ± 0.59+ | 0.50 ± 0.11+ | 3.87 ± 0.44 | 0.32 ± 0.04 |
| 1 Hour | 3.62 ± 0.84+ | 0.80 ± 0.18+ | 5.12 ± 0.65 | 0.46 ± 0.06 |
| 4 Hours | 5.35 ± 0.88 | 2.12 ± 0.35+ | 5.12 ± 0.59 | 0.95 ± 0.14 |
| 24 Hours | 5.59 ± 0.60+ | 6.70 ± 1.42+ | 2.46 ± 0.88 | 1.18 ± 0.47 |

*Mean Percent of Administered Dose Per Organ ± Standard Deviation
Mean of Percent Administered Dose in Pancreas/Percent Injected Dose in Liver ± Standard Deviation
+Significantly Different from HIPDM at p ≤ 0.05

EXAMPLE 9

Pancreatic Uptake of ERC 94

The pancreas uptakes and pancreas/liver ratios of I-125 ERC 94 and I-125 HIPDM were compared in Balb/c mice as described in Example 6. The results are shown in Table 4.

The pancreas uptakes with ERC 94 were lower than those of HIPDM at all time periods studied except 24 hours. However, at all time periods studied from 30 minutes to 24 hours, the pancreas/liver ratios were significantly higher with ERC 94 then with HIPDM.

TABLE 4

Pancreas Uptakes and Pancreas to Liver Ratio in Balb/c Mice
(Six Animals at Each Time Period)

| Time After Administration | ERC 94 | | HIPDM | |
| --- | --- | --- | --- | --- |
| | Pancreas* | P/L# | Pancreas* | P/L# |
| 5 Minutes | 1.56 ± 0.26+ | 0.22 ± 0.04 | 2.64 ± 0.50 | 0.21 ± 0.03 |
| 30 Minutes | 2.86 ± 0.48+ | 0.61 ± 0.06+ | 3.87 ± 0.44 | 0.32 ± 0.04 |
| 1 Hour | 3.45 ± 0.90+ | 0.67 ± 0.19+ | 5.12 ± 0.65 | 0.46 ± 0.06 |
| 4 Hours | 4.65 ± 0.67 | 1.61 ± 0.26+ | 5.12 ± 0.59 | 0.95 ± 0.14 |
| 24 Hours | 3.76 ± 1.62 | 4.03 ± 1.76+ | 2.46 ± 0.88 | 1.18 ± 0.47 |

*Mean Percent of Administered Dose Per Organ ± Standard Deviation
Mean of Percent Administered Dose in Pancreas/Percent Injected Dose in Liver ± Standard Deviation
+Significantly Different from HIPDM at p ≤ 0.05

EXAMPLE 10

Toxicity and Radiation Dosimetry

Toxicity

Animal studies indicate a low chemical toxicity for ERC 9. It was assumed that the maximum human dose of ERC 9 would be 2 mg per 50 kg (or 0.04 μg per gram) body weight. Mouse studies were done at a rate of 500 times the maximum human dose on a weight basis. Five Balb/c male and five Balb/c female mice were injected via the tail vein with 0.005 ml per gram body weight of a solution of ERC 9 in water (4 mg per ml) on each of three occasions one day apart. The animals were maintained for 30 days. There was no indication of immediate or delayed toxicity due to the compound. Histological examination of various organs and tissues indicated no changes that could be attributed to chemical toxicity.

Radiation Dosimetry

The human radiation dose from I-123 ERC 9 was estimated from tissue distribution data in mice.

Male Balb/c mice were injected via the tail vein with I-125 ERC 9 (20 μg, 0.01 MBq, in 0.1 ml). At specific time periods from 5 minutes to 24 hours after administration, six mice were killed by $CO_2$ asphyxiation. Blood samples were taken and various organs were removed. The radioiodine uptake in various organs and tissues was determined by counting in a gamma spectrometric detector. The amount of radioactivity in each organ or tissue was compared to that in a standard of the injected dose. The percent uptake was calculated for each organ of each animal. The mean percent uptake in the organs was calculated for the animals at each time period.

The mean uptakes for each of the organs and tissues were plotted versus time on semilogarithmic paper. From these plots, the uptake and clearance half times for each of the organs and tissues were calculated.

Using these values and the MIRD (Society of Nuclear Medicine) method of dosimetry calculations, the human radiation doses from I-123 were calculated. These indicate that the pancreas will be the critical organ with a radiation dose of approximately 15.5 mGy per 111 MBq of I-123 ERC 9 administered.

EXAMPLE 11

Pancreatic Imaging in Human Subjects

Imaging studies have been done in two human volunteers using I-123 ERC 9.

I-123 ERC 9 (185 MBq, 2 mg), prepared as in Example 2, was injected intravenously into the two volunteers. Using a gamma camera with SPECT (Single Photon Emission Computed Tomography) capability, planar images were obtained at 30 minutes, 1.5 hours, 3 hours and 24 hours after injection. SPECT images were obtained at 3-4 hours after injection.

Uptake of the radiotracer was seen as early as 30 minutes after administration. Optimum pancreatic uptake and pancreas/liver ratio was seen at 3-4 hours. By 24 hours the amount of radioactivity in the pancreas had decreased, by physical decay and biological clearance, to such an extent that visualization of the pancreas was less than optimal although still present.

Figure 2A:
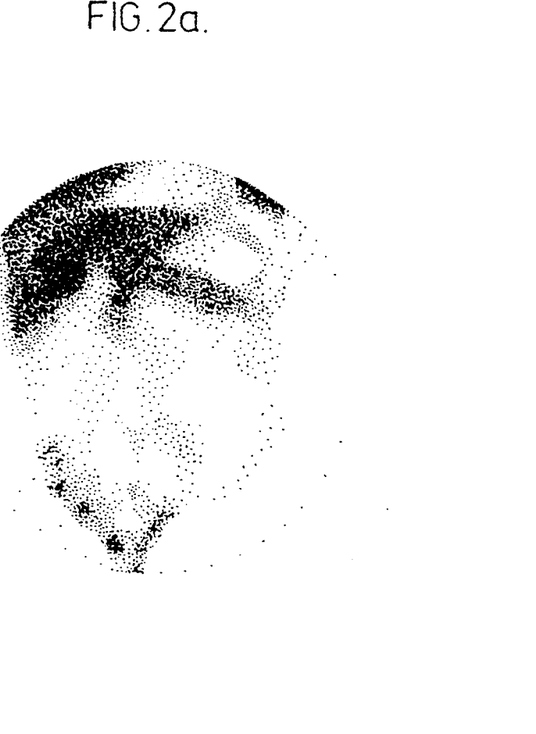
FIG. 2 shows in panel (a) a planar gamma camera image of the human pancreas, and in panel (b) a SPECT gamma camera image obtained using the compounds of the invention.

FIG. 2a shows the planar gamma camera image of the pancreas which was obtained in the first subject three hours after administration of I-123 ERC 9.

Figure 2B:
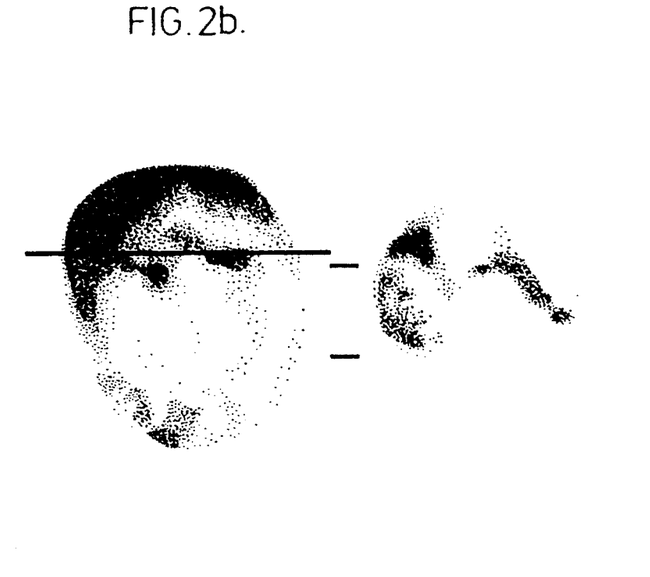

FIG. 2b shows the SPECT gamma camera image of the pancreas in the same subject three to four hours after administration.

Figure 3A:
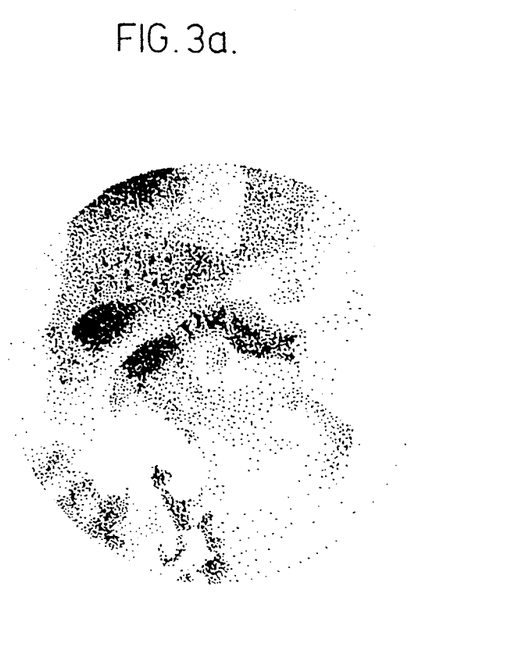
FIG. 3 shows similar images to those in FIG. 2 in a second human subject.
Figure 3B:
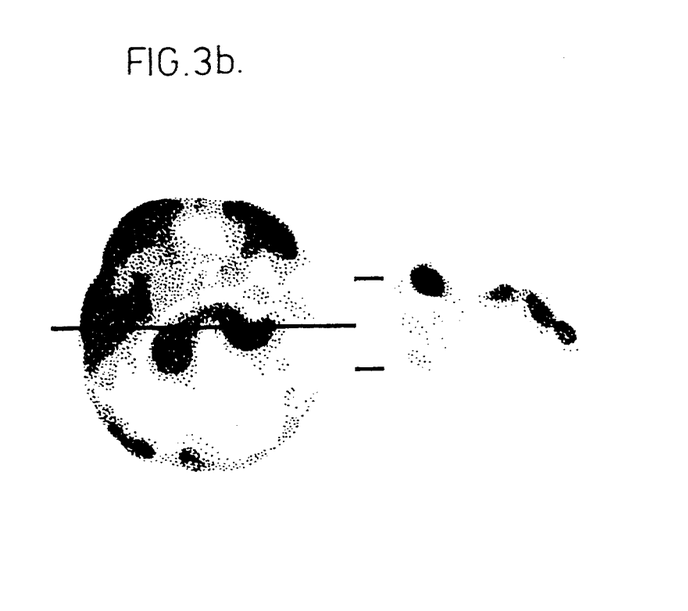

FIGS. 3a and 3b show similar images which were obtained in the second subject at the same time intervals after administration of I-123 ERC 9.

As seen in these figures, both planar and SPECT images show a high degree of accumulation of radiolabel in normal human pancreas and good discrimination of pancreas from other abdominal organs, allowing detection of reduced pancreatic uptake at sites of pancreatic abnormality in disease states and providing a useful diagnostic tool and technique.

Although only preferred embodiments of the present invention have been described, the present invention is not limited to the features of these embodiments, but includes all variations and modification within the scope of the claims.

We claim:

1. A compound effective for pancreatic imaging having the general formula:

wherein n is 3 to 10; $R_1$ and $R_2$ are the same or different and are hydroxyl or lower alkyl having 1 to 6 carbon atoms; $R_3$ is lower alkyl having 1 to 6 carbon atoms; and N' is a nitrogen atom forming part of a 4- to 8-membered heterocyclic ring containing one or two hetero atoms, one of which is said nitrogen, said heterocyclic ring being unsubstituted or substituted with one or more lower alkyl groups and pharmaceutically acceptable acid addition salts thereof.

2. A compound effective for pancreatic imaging having the general formula:

wherein n is 1 to 10; $R_1$ and $R_2$ are the same or different and are hydroxyl or lower alkyl having 1 to 6 carbon atoms; $R_3$ is lower alkyl having 1 to 6 carbon atoms; and N' is a nitrogen atom forming part of a morpholino or pyrrolidino ring which is unsubstituted or substituted with one or more lower alkyl groups and pharmaceutically acceptable acid addition salts thereof.

3. A compound in accordance with claim 1 or 2 wherein I is a radioactive isotope of iodine selected from the group consisting of I-121, I-123, I-125 and I-131.

4. A compound in accordance with claim 1 wherein N' is a nitrogen atom forming part of a morpholino, pyrrolidino or piperidino ring which is unsubstituted or substituted with one or more lower alkyl groups and pharmaceutically acceptable addition salts thereof.

5. A compound in accordance with claim 4 wherein n is 3.

6. A compound in accordance with claim 5 wherein $R_1$ is hydroxyl attached at 2 position of benzene ring of said compound; $R_2$ is lower alkyl having 1 to 6 carbon atoms and attached at 3 position of said benzene ring and I is attached at 5 position of said benzene ring.

7. A compound in accordance with claim 5 wherein said compound is I -N[3(4-morpholino) propyl]-N-methyl-2-hydroxy-3-methyl-5-iodobenzylamine and I is a radioactive isotope of iodine selected from the group consisting of I-121, I-123, I-125 and I-131.

8. A compound in accordance with claim 4 wherein said compound is I-123 N[3(4-morpholino)propyl]-N-methyl-2-hydroxy-3-methyl-5-iodobenzylamine.

9. A compound in accordance with claim 4 wherein said compound is I- N[3(1-pyrrolidino)propyl]-N-methyl-2-hydroxy-3-methyl-5-iodobenzylamine and I is a radioactive isotope of iodine selected from the group consisting of I-121, I-123, I-125 and I-131.

10. A compound in accordance with claim 4 wherein said compound is I-123 N[3(1-pyrrolidino)propyl]-N-methyl-2-hydroxy-3-methyl-5-iodobenzylamine.

11. A compound in accordance with claim 4 wherein said compound is I- N[3(1-piperidino)propyl]-N-methyl-2-hydroxy-3-methyl-5-iodobenzylamine and I is a radioactive isotope of iodine selected from the group consisting of I-121, I-123, I-125 and I-131.

12. A compound in accordance with claim 4 wherein said compound is I-123 N[3(1-piperidino)propyl]-N-methyl-2-hydroxy-3-methyl-5-iodobenzylamine.

* * * * *

UNITED STATES PATENT AND TRADEMARK OFFICE
CERTIFICATE OF CORRECTION

PATENT NO. : 5,349,063

DATED : September 20, 1994

INVENTOR(S) : Joshua et al

It is certified that error appears in the above-identified patent and that said Letters Patent is hereby corrected as shown below:

On title page, item [56] - OTHER PUBLICATIONS:

Column 1, line 1, "Trampesch" should be -- Tramposch --; last line of column 1, Hydroxyl" should be -- Hydroxy --; column 2, line 2, "1987" should be -- 1983 --; column 2, line 8, "1989" should be -- 1990 --.

Column 1, line 4, after "continuation" omit the comma (,).

Column 3, line 17, before "Acetaldehyde" insert -- † --.

Column 4, line 4, "Pyrrolidino" should be -- pyrrolidino --.

Column 8, line 51, "0,467" should be -- 0.467 --.

Column 9, line 39, "1,945" should be -- 1.945 --.

Column 9, line 40, "J-6" should be -- J=6 --.

Column 11, line 61, "0,005" should be -- 0.005 --.

UNITED STATES PATENT AND TRADEMARK OFFICE
CERTIFICATE OF CORRECTION

PATENT NO. : 5,349,063
DATED : September 20, 1994
INVENTOR(S) : Joshua, et al

It is certified that error appears in the above-indentified patent and that said Letters Patent is hereby corrected as shown below:

Column 14:
        Claims 8,9,10, 11 and 12 should be dependent upon claim 5.

Signed and Sealed this

Twenty-ninth Day of November, 1994

Attest:

BRUCE LEHMAN

*Attesting Officer*    *Commissioner of Patents and Trademarks*